United States Patent
Ebert et al.

(10) Patent No.: US 10,500,215 B2
(45) Date of Patent: *Dec. 10, 2019

(54) FORMULATIONS AND METHODS FOR PROVIDING PROGESTIN-ONLY CONTRACEPTION WHILE MINIMIZING ADVERSE SIDE EFFECTS ASSOCIATED THEREWITH

(71) Applicant: Allergan Sales, LLC, Irvine, CA (US)

(72) Inventors: Charles Ebert, Salt Lake City, UT (US); Gary Hoel, Salt Lake City, UT (US); Angela Anigbogu, Salt Lake City, UT (US); Samir Roy, Salt Lake City, UT (US)

(73) Assignee: Allergan Sales, LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/162,670

(22) Filed: Oct. 17, 2018

(65) Prior Publication Data

US 2019/0111063 A1    Apr. 18, 2019

Related U.S. Application Data

(63) Continuation of application No. 11/205,297, filed on Aug. 15, 2005, now Pat. No. 10,137,135.

(51) Int. Cl.
*A61K 9/70*      (2006.01)
*A61K 31/565*    (2006.01)
*A61K 31/57*     (2006.01)

(52) U.S. Cl.
CPC ............ *A61K 31/57* (2013.01); *A61K 9/7061* (2013.01); *A61K 31/565* (2013.01)

(58) Field of Classification Search
CPC ..... A61K 31/57; A61K 31/565; A61K 9/7061
See application file for complete search history.

(56) References Cited

U.S. PATENT DOCUMENTS

| | | | |
|---|---|---|---|
| 3,472,931 A | 10/1969 | Stoughton | |
| 3,551,154 A | 12/1970 | Bias et al. | |
| 4,006,218 A | 2/1977 | Sipos | |
| 4,820,720 A | 4/1989 | Sanders et al. | |
| 4,849,224 A | 7/1989 | Chang et al. | |
| 4,855,294 A | 8/1989 | Patel et al. | |
| 4,973,468 A | 11/1990 | Chiang et al. | |
| 4,983,395 A | 1/1991 | Chang et al. | |
| 5,006,342 A | 4/1991 | Cleary et al. | |
| 5,122,383 A | 6/1992 | Heiber et al. | |
| 5,152,997 A | 10/1992 | Ebert et al. | |
| 5,164,190 A | 11/1992 | Patel et al. | |
| 5,211,952 A | 5/1993 | Spicer et al. | |
| 5,212,199 A | 5/1993 | Heiber et al. | |
| 5,227,169 A | 7/1993 | Heiber et al. | |
| 5,460,820 A | 10/1995 | Ebert et al. | |
| 5,601,839 A | 2/1997 | Quan et al. | |
| 5,622,943 A | 4/1997 | Hodgen | |
| 5,626,866 A | 5/1997 | Ebert et al. | |
| 5,770,219 A | 6/1998 | Chiang et al. | |
| 5,780,050 A | 7/1998 | Jain et al. | |
| 5,783,208 A | 7/1998 | Venkateshwaran et al. | |
| 5,980,932 A | 11/1999 | Chiang et al. | |
| 5,985,317 A | 11/1999 | Venkateshwaran et al. | |
| 6,149,935 A | 11/2000 | Chiang et al. | |
| 6,465,005 B1 | 10/2002 | Biali et al. | |
| 2002/0016316 A1 | 2/2002 | Hill et al. | |
| 2003/0152613 A1 | 8/2003 | Houze | |
| 2003/0152614 A1 | 8/2003 | Houze | |
| 2003/0152615 A1 | 8/2003 | Houze | |
| 2004/0037873 A1 | 2/2004 | Anigbogu | |
| 2005/0058695 A1 | 3/2005 | Anigbogu et al. | |
| 2006/0009428 A1 | 1/2006 | Grubb et al. | |
| 2006/0057186 A1 | 3/2006 | Heller | |

FOREIGN PATENT DOCUMENTS

| | | |
|---|---|---|
| EP | 0043738 | 1/1982 |
| WO | 0117472 | 3/2001 |
| WO | 021023900 | 12/2002 |
| WO | 2002102390 | 12/2002 |

OTHER PUBLICATIONS

R. Rivera et al., "The Mechanism of Action of Hormonal Contraceptives and Intrauterine Contraceptive Devices", AJOG Reviews, 1999, 181 {5, Part 1): 1263-69.
S.W. Wright et al., "Effect of Daily Small Doses of Norgestrel on Ovarian Function", J. Obstet Gyn Br Commonw, 1970, 77:65-68.
E.G. Raymond et al., "Contraceptive Efficacy, Pharmacokinetics, and Safety of Annuelle® Biodegradable Norethindrone Pellet Implants", Fertil and Steril, 1996, 66{6}:954-61.
G.S. Grubb, "A Comparative Evaluation of the Safety and Contraceptive Effectiveness of 65 mg and 100 mg of 90-Day Norethindrone (NET) Injectable Microspheres: A Multicenter Study", Fertil and Steril, 1989, 51{5}:803-810.
World Health Organization, "Laboratory Manual for the Examination of Human Semen and Sperm-Cervical Mucus Interaction", 4th Ed., Cambridge, U.K., Cambridge University Press, 1999.
G.N. Gupta et al., "Multicenter Clinical Trial of Implanted Norethindrone Pellets for Long-Acting Contraception in Women", Contraception, 1984, 30:239-52.
K.D. LaGuardia et al., "Efficacy, Safety and Cycle Control of Five Oral Contraceptive Regimens Containing Norgestimate and Ethinyl Estradiol", Contraception, 2003, 67:431-37.
M. Zieman et al., "Contraceptive Efficacy and Cycle Control with the Ortho Evra™/Evra™ Transdermal System: the Analysis of Pooled Data", Fertil and Steril, 2002, 77{2}(suppl 2):S13-S18.
R.T. Burkman, "The Transdermal Contraceptive Patch: A New Approach to Hormonal Contraception", 2002, Int J Fertil, 47{2}: 69-76.

(Continued)

*Primary Examiner* — Barbara P Badio
(74) *Attorney, Agent, or Firm* — Florek & Endres PLLC

(57) ABSTRACT

Formulations and methods for providing progestin-only contraception to a woman while minimizing various side effects, such as breakthrough bleeding, that are normally associated with progestin-only contraception are disclosed and described. In one aspect, the method can include transdermally administering a formulation having a contraceptively effective amount of a single progestin as the sole active hormonal agent to the woman as part of a contraceptive regimen.

21 Claims, No Drawings

(56) References Cited

OTHER PUBLICATIONS

U.M. Joshi et al., "Phase I Comparative Trial With Subdermal Implants—Bioabsorbable Levonorgesterel or Norethisterone Pellet Fused With Cholesterol", Contraception, 1985, 31{1}: 71-82.

G.K. McEvoy (ed.), Contraceptives, 68:12: Progestins, AHFS Drug Information, Bethesda, MD, American Society of Health-System Pharmacists, 2002, 2964-66.

A. Del Conte et al., "Cycle Control With Oral Contraceptives Containing 20ug of Ethinyl Estradiol", Contraception, 1999, 59:187-93.

A.N. Poindexter et al., "Cycle Control, Tolerability, and Satisfaction Among Women Switching From 30-35 ug Ethinyl Estradiol-Containing Oral Contraceptives to the Triphasic Norgestimate/25 ug Ethinyl Estradiol-Containing Oral Contraceptive Ortho Tri-Cyclen® Lo", Inti J Fertil, 2003, 48{4}: 163-72.

J.W. Goldzieher, "Pharmacology of Contraceptive Steroids: A Brief Review", Am J Obstet Gyn, 1989,160:1260-64.

M.F. McCann et al., "Progestin-Only Oral Contraception: A Comprehensive Review", Contraception, 1994, 50{suppl 1):S9-S195.

F.Z. Stanczyk et al., "A Radioimmunoassay for Norethindrone (NET): Measurement of Serum NET Concentrations Following Ingestion of NET-Containing Oral Contraceptive Steroids", Contraception, 1978, 18:615-633.

D.J. Back et al., "Kinetics of Norethindrone in Women. II. Single-Dose Kinetics", Clin Pharmacol Ther, Oct. 1978, 24{4):448-53.

L.W. Young, Written Opinion of the International Searching Authority in PCT/US06/31592, dated Mar. 29, 2007, 4 pages, USPTO, Alexandria, VA.

P. Becamel, International Preliminary Report on Patentability in PCT/US06/31592, dated Feb. 20, 2008, 5 pages, International Bureau of WIPO, Geneva, Switzerland.

L.W. Young, International Search Report in PCT/US06/31592, dated Jul. 30, 2007, 2 pages, USPTO, Alexandria, VA.

Singh,et al., Biodegradable Norethindrone (NET: Cholesterol) Contraceptive Implants: Phase II-A: A Clinical Study in Women, 1997, Contraception, pp. 23-33, vol. 55.

Li, C. et al., The Study of Transdermal Administration of Ace Inhibitors and Improved Absorption of Their Prodrugs, (Nov. 2, 2000) (Abstract only).

Houze et al. "In-Vitro Transdermal Permeation Performance of Drug and Pro-Drug Combinations," (Nov. 14, 2002) (Abstract).

Budavari, Susan (Editor) et al. "The Merck Index" 1996, Published by Merck Research laboratories, Whitehouse Station, New Jersey, p. 1149.

Gennaro, Alfonso R. (Editor), "Remington: The Science and Practice of Pharmacy," 20,n Edition, p. 1096, 1386-1388.

Ebert et al. Declaration, Aug. 17, 2010.

FORMULATIONS AND METHODS FOR PROVIDING PROGESTIN-ONLY CONTRACEPTION WHILE MINIMIZING ADVERSE SIDE EFFECTS ASSOCIATED THEREWITH

This application is a continuation of U.S. patent application Ser. No. 11/205,297 filed on Aug. 15, 2005.

FIELD OF THE INVENTION

The present invention relates to formulations and methods for effective contraception while minimizing or reducing adverse side effects associated with progestin-only contraception, such as breakthrough bleeding. Accordingly, this invention involves the fields of pharmaceutical sciences, medicine, chemistry and other health sciences.

BACKGROUND OF THE INVENTION

Progesterone is a primary progestational substance produced by ovarian cells of the corpus luteum. Progestins, e.g., progesterone and its derivatives, transform the proliferative endometrium into secretory endometrium. This change in the endometrium is essential to the implantation of a fertilized ovum and the development of a placenta during conception and the early stages of pregnancy. Many of these changes require, however, the presence of estrogen. Therefore, in the absence of estrogen, progestins can exert an atrophic effect on the endometrium, as well as various other contraceptive effects. Such contraceptive effects may vary depending on the concentration and the nature of the particular progestin involved.

Accordingly, various progestins have been utilized as contraceptive drugs due to their convenient nature coupled with their fairly predictable ovulatory and progestational effects. One specific progestin that has received much attention is norethindrone (NE) and its prodrug norethindrone acetate (NEA). Both compounds have been orally and transdermally administered as part of a number of specific formulations. Though the actions of these and other progestins can vary, many exert effects on the ovaries, the endometrium, and the cervix. For example, certain long acting injectable progestins in appropriate doses can cause endometrial atrophy. Oral preparations can vary according to the drug and the dose. Some permitting a normal endometrium and others causing regression. Progestins can also inhibit ovulation by suppressing the ovarian response to gonadotropins. This may cause a failure to ovulate or, if ovulation does occur, a smaller hyposecreting corpus luteum. Particularly high doses of progestins tend to suppress the pituitary release of lutenizing hormone and the hypothalamic release of gonadotropin releasing hormone (GnRH), which can act to prevent ovulation through decreased gonadotropin output. Progestins also tend to increase the viscosity of cervical mucous secretions and therefore impede the mobility of sperm. These and other actions of progestins can act in combination to provide effective contraception.

One undesirable issue with the use of oral progestin-only contraception is the need for consistent dosing at the same time each day. The onset of cervical mucus thickening typically occurs within about 2 hours of dosing and lasts for about 16 to 19 hours. By about 24 hours post dose, the cervical mucus returns to substantially normal viscosity. Since thickening of cervical mucus is such an important factor in attaining the progestin-induced contraceptive effect, it is extremely important that dosing take place substantially 24 hours apart in order to maintain the elevated mucus viscosity. Of course, such a stringent dosing regimen is inconvenient and runs a high risk of non-compliance.

Additionally, progestin-only contraception tends to induce certain adverse side effects. One of the most inconvenient of such side effects is spotting and breakthrough bleeding. Such bleeding can be unpredictable or irregular in onset, and in some cases bleeding can be more voluminous than in regular menstruation. Such effects can often weigh heavily against the supposed convenience of this form of birth control.

Therefore, formulations and methods for progestin-only contraception which minimize the incidence of adverse side effects, particularly spotting and breakthrough bleeding, continue to be sought.

SUMMARY OF THE INVENTION

Accordingly, the present invention discloses methods of providing effective progestin-only contraception to a woman while minimizing adverse side effects that are normally associated with progestin-only contraception. Such adverse side effects include, without limitation, strokes, myocardial infarctions, embolisms, breakthrough bleeding, etc. In one aspect, such a method can include transdermally administering a formulation having a contraceptively effective amount of a single progestin as the sole active hormonal agent to the woman.

A variety of progestins may be used as the active agent in the formulations and methods of the present invention. Specific examples of progestins may include without limitation, progesterone, hydroxyprogesterone, megestrol acetate, dimethisterone, norgestrel, levonorgestrel, medroxyprogesterone acetate, desogestrel, norgestimate, ethynodiol diacetate, norethindrone, norethindrone acetate, and norethynodrel, including their active metabolites and derivatives. In one specific aspect, the progestin can be or consist of progesterone. In another aspect, the progestin can include or consist of norethindrone. In another aspect, the progestin can include or consist of norethindrone acetate. In yet another aspect, the progestin can include or consist of norethynodrel.

The formulations of the present invention may include various dosages of progestins to achieve a therapeutic effect. For example, in one aspect the progestin may be either norethindrone or norethindrone acetate administered at a rate and an amount that provides a minimum norethindrone serum level of at least about 160 pg/ml in order to cause and sustain physiologic events in the woman resulting in contraception, while at the same time providing a maximum norethindrone serum level of less than about 2400 pg/ml in order to avoid a significant incidence of adverse side effects. In another aspect, the maximum norethindrone serum level may be from about 240 pg/ml to about 1920 pg/ml. In yet another aspect, the maximum norethindrone serum level may be from about 300 pg/ml to about 1200 pg/ml. In a further aspect, the maximum norethindrone serum level can be from about 400 pg/ml to about 1100 pg/ml. In one aspect, the minimum norethindrone serum level can be at least about 300 pg/ml. In yet another aspect, the minimum norethindrone serum level can be at least about 350 pg/ml.

Various physiologic events resulting from the administration of a progestin are believed to contribute to contraception. Such physiologic events may include, without limitation, suppression of ovulation, a thickening of cervical mucus, and combinations thereof. Contraceptive physiologic events can be sustained for varying amounts of time following the initial administration, depending on the dosage form, the nature of any penetration enhancer present, the amount of progestin in the formulation, etc. In one aspect, physiologic events may be sustained for a period of up to at least 168 hours. In another aspect, physiologic events associated with contraception may be sustained for a period from about 24 hours to about 168 hours. In yet another aspect, contraception may be sustained for a period of from about 24 hours to about 96 hours. In a further aspect, contraception may be sustained for a period of from about 48 hours to about 168 hours.

As such, either norethindrone or norethindrone acetate may also be administered at a rate and an amount that provides a minimum norethindrone serum level sufficient to cause and sustain contraception for a period of from about 24 hours to about 168 hours and which avoids a significant incidence of adverse side effects by attaining a maximum norethindrone serum level that is less than about 2400 pg/ml.

In addition to the progestin, the transdermal formulations of the present invention may optionally include various additional additives of a non-hormonal nature. For example, delivery of the progestin may be improved by utilizing one or more permeation enhancers. As such, the formulations can include a permeation enhancer. In one aspect, the permeation enhancer can include, or consist of a sorbitan ester-type enhancer. One example of a sorbitan ester-type enhancer is, without limitation, sorbitan monooleate. In another aspect, the permeation enhancer can include a lauryl-type enhancer. Examples of lauryl type enhancers may include, without limitation, lauryl alcohol, 1-lauryl-2-pyrrolidone, and mixtures thereof. In yet another aspect, the permeation enhancer may include a combination of lauryl alcohol an isopropyl myristate. In a further aspect, the permeation enhancer may include a polyol-type enhancer, such as dipropylene glycerol. While the amount of penetration enhancer used may vary depending on a number of criteria, such as the type of enhancer selected, the material of the carrier, etc., in one aspect, the enhancer amount may be from about 0.01% w/w to about 50% w/w of the transdermal composition. In another aspect, the enhancer amount may be from about 3% w/w to about 15% w/w of the transdermal composition.

In one specific aspect of the present invention, a method of providing progestin-only contraception to a woman while minimizing adverse side effects associated with progestin-only contraception is provided. The method may include transdermally administering a formulation having norethindrone acetate as the sole active hormonal ingredient in an amount of from about 5% w/w to about 25% w/w of the transdermal formulation and a permeation enhancer in an amount from about 0.01% w/w to about 50% w/w of the transdermal formulation. The formulation may be administered at a rate and an amount that provides a minimum norethindrone serum level of at least 200 pg/ml in order to cause and sustain physiologic events in the woman resulting in contraception for a period of from about 24 hours to about 168 hours, and also provide a maximum norethindrone serum level of less than about 2400 pg/ml in order to avoid a significant incidence of adverse side effects. The maximum norethindrone serum level may be obtained from about 24 to about 96 hours following administration.

In another aspect of the present invention, a method of providing progestin-only contraception to a woman while minimizing adverse side effects associated with the progestin-only contraception is provided. The method may include transdermally administering a formulation having either norethindrone or norethindrone acetate as the sole active hormonal agent to the woman, at a rate and an amount that provides a minimum norethindrone serum level sufficient to cause and sustain contraception for a period of from about 24 to about 168 hours and which maintains a maximum norethindrone serum level that may be up to about 15 times greater than the minimum norethindrone serum level. In yet another aspect, the maximum norethindrone serum level may be up to about 8 times greater than the minimum norethindrone serum level. In a further aspect, the maximum norethindrone serum level may be up to about 4 times greater than the minimum norethindrone serum level. In yet another aspect, the maximum norethindrone serum level may be up to about 2.75 times greater than the minimum norethindrone serum level.

The present invention additionally encompasses various kits, formulations, and articles of manufacture to be used in providing progestin-only contraception to a woman while minimizing adverse side effects, such as breakthrough bleeding, associated with progestin-only contraception. In one aspect, such a kit may include a transdermally administrable formulation including norethindrone acetate as the sole active agent in an amount of from about 5% w/w to about 25% w/w of the transdermal formulation and a permeation enhancer in an amount of from about 0.01% w/w to about 50% w/w of the transdermal formulation. The formulation may be administered at a rate and an amount that provides a minimum norethindrone serum level of at least 160 pg/ml in order to cause and sustain physiologic events in the woman resulting in contraception for a period of from about 24 hours to about 168 hours, and also may provide a maximum norethindrone serum level of less than about 2400 pg/ml, which is obtained from about 24 to about 96 hours following administration, in order to avoid a significant incidence of adverse side effects. The kit may also include a set of instructions describing a method of using the transdermally administrable formulation.

Numerous transdermal dosage forms are contemplated for use with the present invention. For example, in one aspect the kit can contain a formulation having a dosage form selected from the group consisting of transdermal patches, ointments, lotions, gels, pastes, mousses, aerosols, creams, gels, and combinations thereof. In one aspect, the formulation may be in a transdermal patch dosage form, and the kit may include at least three patches to be administered for up to about 168 hours. The kit may also contain a placebo patch.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying claims, or may be learned by the practice of the invention.

DETAILED DESCRIPTION

A. Definitions

In describing and claiming the present invention, the following terminology will be used in accordance with the definitions set forth below.

The singular forms "a," "an," and, "the" include plural referents unless the context clearly dictates otherwise. Thus, for example, reference to "an adhesive" includes reference to one or more of such adhesives, and reference to "an excipient" includes reference to one or more of such excipients.

The terms "progestin" or "progestogen" refer to any natural or synthetic progestational substance that mimics some or all of the actions of progesterone. "Progestin" and "progestogen" may also refer to any natural or synthetic substance that exerts a biological or pharmacological action primarily by binding to progestin receptors. Examples include, but are not limited to, progesterone, medroxyprogesterone acetate, hydroxyprogesterone, megestrol acetate, dimethisterone, norgestrel, levonorgestrel, desogestrel, norgestimate, ethynodiol diacetate, norethynodrel, norethindrone, and norethindrone acetate, esters, derivatives, prodrugs, active metabolites, and isomers thereof. Progestins have been administered to women in order to provide effective contraception. While the amount of a progestin required to achieve this effect vary from woman to woman, methods for determining appropriate or effective amounts for the purpose of contraception are well known to those of ordinary skill in the art. Progestins themselves are well known in the art, a partial description of which can be found on pgs. 1386-1388 of *Remington: The Science and Practice of Pharmacy* (20$^{th}$ ed. 2000), which is incorporated herein by reference.

As used herein in, "norethindrone," or "NE" refers to a compound having the general chemical structure:

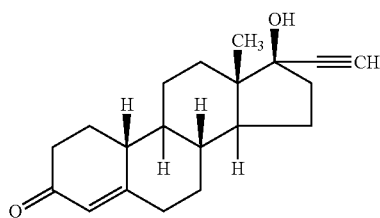

Norethindrone is well known in the art, and is listed as monograph 6790 on pg. 1149 of the *Merck Index* (12$^{th}$ ed. 1996), which is incorporated herein by reference.

As used herein, "norethindrone acetate," or "NEA" refers to a compound having the general chemical structure:

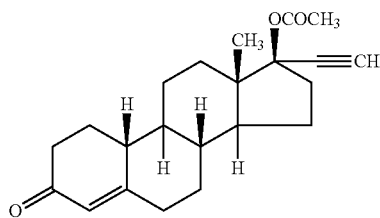

Norethindrone acetate is well known in the art as an ester type prodrug of norethindrone and is described on pg. 1096 of *Remington: The Science and Practice of Pharmacy* (19" ed. 1995), which is incorporated herein by reference.

The terms "breakthrough bleeding" and "intermenstral bleeding" can be used interchangeably, and are defined as any vaginal bleeding occurring during the menstrual cycle of a woman on hormonal contraceptives, excluding contiguous bleeding with menses. Breakthrough bleeding can include any discernable vaginal bleeding, including spotting.

As used herein, "subject" refers to a mammal that may benefit from the administration of a drug composition or method of this invention. Examples of subjects include humans, especially females, and may also include other animals such as horses, pigs, cattle, dogs, cats, rabbits, and aquatic mammals.

As used herein, the terms "formulation" and "composition" are used interchangeably and refer to a mixture of two or more compounds, elements, or molecules. In some aspects the terms "formulation" and "composition" may be used to refer to a mixture of an active agent with a carrier or other excipients. The terms "drug," "pharmaceutical," "active agent," and "bioactive agent" are also used interchangeably to refer to a pharmacologically active substance or composition. These terms of art are well-known in the pharmaceutical and medicinal arts.

As used herein, "transdermal refers to the route of administration taken by a drug that is applied to and absorbed through an area of skin. In some aspects, the skin may be substantially unbroken. Thus the terms "transdermal formulation" and "transdermal composition" can be used interchangeably, and refer to formulations or compositions that are applied to a surface of the skin and transdermally absorbed. Examples of transdermal formulations include but are not limited to, ointments, creams, gels, transdermal patches, sprays, lotions, mousses, aerosols, nasal delivery systems, pulmonary delivery systems, buccal and sublingual delivery systems, vaginal rings, and pastes. The term "transdermal administration" thus refers to the transdermal application of a formulation or composition. Transdermal administration can be accomplished by applying, pasting, rolling, attaching, pouring, pressing, rubbing, spraying, etc., of a transdermal preparation or formulation onto a skin surface. These and additional methods of administration are well known in the art.

The terms "transdermal delivery system," "transdermal patches" or simply "patches" refer to a matrix or liquid reservoir type of transdermal delivery device which is used to transdermally deliver defined doses of a substance, over a specific application period.

By the term "matrix", "matrix system", or "matrix patch" is meant a composition comprising an effective amount of a drug dissolved or dispersed in a polymeric phase, often a pressure sensitive adhesive, which may also contain other ingredients, such as a permeation enhancers, skin irritation reducing agents, excipients, plasticizers, emollients, and other optional ingredients. This definition is meant to include embodiments wherein such polymeric phase is laminated to a pressure sensitive adhesive or used within an overlay adhesive.

One example of a transdermal patch for administering a progestin in accordance with this invention is a matrix-type patch which comprises an occlusive backing that is impermeable to the progestin and defines the face or top surface of the patch and a solid or semisolid matrix layer comprised of a homogeneous blend of the hormone, a polymeric pressure sensitive adhesive carrier, and optionally one or more skin permeation enhancers. Matrix patches are known in the art of transdermal drug delivery. Examples without limitation, of adhesive matrix transdermal patches are those described or referred to in U.S. Pat. Nos. 5,985,317, 5,783, 208, 5,626,866, 5,227,169, 5,122,383, and 5,460,820 which are incorporated by reference in their entirety.

Another example of a transdermal patch for administering a progestin in accordance with this invention is a liquid reservoir system (LRS) type patch which comprises progestin and other optional ingredients, such as a permeation enhancer, in a carrier vehicle. The carrier vehicle comprises a fluid of desired viscosity, such as a gel or ointment, which is formulated for confinement in a reservoir having an impermeable backing and a skin contacting permeable membrane, or membrane adhesive laminate providing diffusional contact between the reservoir contents and the skin. For application, a peelable release liner is removed and the patch is attached to the skin surface. LRS patches are known in the art of transdermal drug delivery. Examples without limitation, of LRS transdermal patches are those described or referred to in U.S. Pat. Nos. 4,849,224, 4,983,395, which are incorporated by reference in their entirety.

The terms "skin," "skin surface," "derma," "epidermis," and similar terms are used interchangeably herein, and refer to not only the outer skin of a subject comprising the epidermis, but also to mucosal surfaces to which a drug composition may be administered. Examples of mucosal surfaces include the mucosal of the respiratory (including nasal and pulmonary), oral (mouth and buccal), vaginal, introital, labial, and rectal surfaces. Hence the terms "transdermal" encompasses "transmucosal" as well.

As used herein, "enhancement," "penetration enhancement," or "permeation enhancement," refer to an increase in the permeability of the skin to a drug, so as to increase the rate at which the drug permeates through the skin. Thus, "permeation enhancer," "penetration enhancer," or simply "enhancer" refers to an agent, or mixture of agents that achieves such permeation enhancement. Several compounds have been investigated for use as penetration enhancers. See, for example, U.S. Pat. Nos. 5,601,839; 5,006,342; 4,973,468; 4,820,720; 4,006,218; 3,551,154; and 3,472,931. An index of permeation enhancers is disclosed by David W. Osborne and Jill J. Henke, in their publication entitled "Skin Penetration Enhancers Cited in the Technical Literature." published in *Pharmaceutical Technology* (June 1998), which is incorporated by reference herein.

As used herein, "effective amount of an enhancer refers to an amount sufficient to increase the penetration of a drug through the skin. Methods for assaying the characteristics of permeation enhancers are well-known in the art. See, for example, Merritt et al., "Diffusion Apparatus for Skin Penetration. *J. of Controlled Release* 61 (1984), incorporated herein by reference in its entirety. Thus, an "effective amount" or a "therapeutically effective amount" of a drug refers to a non-toxic, but sufficient amount of the drug, to achieve therapeutic results in treating a condition for which the drug is known to be effective. It is understood that various biological factors may affect the ability of a substance to perform its intended task, and that an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a somewhat subjective decision. Generally speaking, the determination of an effective amount is well within the ordinary skill in the art of pharmaceutical Sciences and medicine. See, for example, Meiner and Tonascia, "Clinical Trials: Design, Conduct, and Analysis." *Monographs in Epidemiology and Biostatistics*, Vol. 8 (1986), incorporated herein by reference.

A "contraceptively effective amount" refers to the minimum amount of drug sufficient to produce a contraceptive effect in a subject. The determination of a contraceptively effective amount of a drug is well-within the ordinary skill in the art of pharmaceutical and medical sciences.

As used herein, "serum level" refers to the level of a drug in the blood of a subject. A therapeutically effective serum level may vary depending on the therapeutic benefit desired, as well as other variables such as the subject's age, weight, metabolism, physiological conditions such as gastrointestinal motility, renal clearance, etc. Therapeutically effective serum levels may be achieved in one or more administrations, applications or dosages. As used herein, "serum level" is used interchangeably with terms such as blood concentration, plasma level, plasma concentration, blood level, serum concentration, serum blood level, serum blood concentration, etc.

As used herein, "pharmaceutically acceptable carrier," and "carrier" may be used interchangeably, and refer to any inert and pharmaceutically acceptable material that has substantially no biological activity, and makes up a substantial part of the formulation. The carrier may be polymeric, such as an adhesive, or non-polymeric and is generally admixed with other components of the composition (e.g., drug, binders, fillers, penetration enhancers, anti-irritants, emollients, lubricants, etc., as needed) to comprise the formulation.

The term "admixed" means that a drug and/or enhancer can be dissolved, dispersed, suspended, or otherwise combined with a carrier.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 micron to about 5 microns" should be interpreted to include not only the explicitly recited values of about 1 micron to about 5 microns, but also include individual values and sub-ranges within the indicated range. Thus, included in this numerical range are individual values such as 2, 3, and 4 and sub-ranges such as from 1-3, from 2-4, and from 3-5, etc.

This same principle applies to ranges reciting only one numerical value. Furthermore, such an interpretation should apply regardless of the breadth of the range or the characteristics being described.

B. The Invention

The present invention involves methods and formulations for effecting progestin-only contraception in a woman in a manner that reduces or minimizes various adverse side effects known as problematic to progestin-only contraception and further increases the convenience of the contraceptive regimen and decreases the risk of pregnancy through dosing non-compliance. Specifically, the Applicants have discovered a surprising relationship between contraceptive effectiveness, side effects, and the dosage form of the progestin formulation. They have found that when serum levels sufficient to provide a contraceptive effect are obtained by transdermal administration of a progestin that various adverse side effects such as breakthrough bleeding are minimized, especially as compared to an equivalent amount of the same progestin administered orally. Further, Applicants have discovered that transdermal administration of progestins for contraceptive purposes virtually eliminates the risk of day-to-day dosing non-compliance, which is significant with oral progestin-only contraception as each pill must be taken at the same time each day.

In practice, transdermal progestin administration is able to provide a minimum drug serum level and reduce or avoid serum concentration "peaks" or "spikes" typically associated with oral progestin therapies. It is believed that peaks may significantly contribute to the incidence of side effects such as break through bleeding, and that by avoiding these peaks through the transdermal administration of a progestin, side effects may be minimized. Additionally, unlike oral therapies, peak drug serum levels can be reduced while minimum drug serum levels are maintained above a threshold level in order to ensure a contraceptive effect in the subject. A similar reduction in peak drug serum levels in oral therapies typically also facilitates a concomitant reduction in minimum drug serum levels thus posing a risk of noneffectiveness.

Accordingly, various transdermal formulations and compositions that contain a contraceptively effective amount of a progestin to be administered to a woman as part of a progestin-only contraceptive regimen are disclosed and described herein. Various progestin-only formulations and articles of manufacture, including kits containing such, are thus contemplated, and are considered to be within the scope of the present invention. Furthermore, methods of minimizing adverse side effects known to be associated with progestin-only contraception by utilizing such formulations are also disclosed and described. Such adverse side effects include, without limitation, strokes, myocardial infarctions, embolisms, breakthrough bleeding, and combinations thereof.

A wide variety of contraceptively effective progestins known to those of ordinary skill in the art can be utilized as the contraceptively active agent in the transdermal formulations of the present invention. Examples of such progestins can include, without limitation, progesterone, hydroxyprogesterone, megestrol acetate, dimethisterone, norgestrel, levonorgestrel, medroxyprogesterone acetate, desogestrel, norgestimate, ethynodiol diacetate, norethindrone, norethindrone acetate, norethynodrel and derivatives thereof. In one aspect, the progestin is progesterone. In another aspect, the progestin is norethindrone. In another aspect, the progestin is norethindrone acetate. In yet another aspect, the progestin is norethynodrel. As the formulation is for progestin-only contraception, other non-progestin type steroids or active agents that contribute to contraception will generally not be included with the selected progestin in the transdermal formulation. Further, most often only a single progestin will be used in the formulation. However, in some circumstances two or more progestins, especially progestins of different type, may be combined in order to achieve a specific formulation.

The amount of progestin to be administered may be measured according to several different parameters. In one aspect, the rate or amount of progestin administered may be a rate or an amount sufficient to achieve a contraceptive effect. The amount required to obtain a contraceptive effect may vary depending on a number of factors, including the activity or potency of the specific progestin selected, as well as physiological variations among women as to drug tolerance and general metabolic issues. In one aspect, ovulation, or a lack thereof, can provide some measure of contraceptive effectiveness. In some cases, serum levels of progesterone ≤3.0 ng/ml are considered to indicate a lack of ovulation. It should be noted, however, that ovulation is highly variable among different subjects, and as such, the ≤3.0 ng/ml level may not be indicative of ovulation in all women. It has been demonstrated that progestins are contraceptively effective even though a large proportion of women ovulate while taking them. In another aspects, inter alfa, thickening of the cervical mucus, suppression of lutenizing hormone (LH) and follicle stimulating hormone (FSH) peaks, reduction of ciliary activity in the fallopian tubes, and certain alterations of the endometrium may also be indicators of contraceptive effectiveness. As such, it is well within the knowledge of those skilled in the art to determine contraceptive effectiveness. In one aspect, at least about 0.35 mg/day of a progestin such as norethindrone or norethindrone acetate can be administered to achieve contraceptive effectiveness. In another aspect, at least about 0.30 mg/day can be administered. In yet another aspect, at least about 0.25 mg/day can be administered. In yet another aspect, from about 0.25 mg/day to about 4.0 mg/day can be administered.

The rate or amount of a progestin to be delivered can also be measured according to serum levels. In one embodiment, the progestin may be either norethindrone or norethindrone acetate administered at a rate and an amount that provides a minimum norethindrone serum level that is sufficient to cause and sustain physiologic events in the woman resulting in contraception, while at the same time providing a maximum norethindrone serum level that avoids a significant incidence of adverse side effects. Various maximum norethindrone serum levels are contemplated that may avoid such adverse side effects. In one aspect, the maximum norethindrone serum level may be less than about 2400 pg/ml. In another aspect, the maximum norethindrone serum level may be from about 240 pg/ml to about 1920 pg/ml. In yet another aspect, the maximum norethindrone serum level may be from about 300 pg/ml to about 1200 pg/ml. In a further aspect, the maximum norethindrone serum level can be from about 400 pg/ml to about 1100 pg/ml. Additionally, various minimum norethindrone serum levels are contemplated that may be sufficient to cause and sustain physiologic events in the woman resulting in contraception. In one aspect, the minimum norethindrone serum level can be at least about 160 pg/ml. In another aspect, the minimum norethindrone serum level can be at least about 300 pg/ml. In yet another aspect, the minimum norethindrone serum level can be at least about 350 pg/ml.

Serum levels can also be expressed in terms of a relationship between the maximum and minimum values. For example, in one aspect the maximum norethindrone serum level that may be up to about 15 times greater than the minimum norethindrone serum level. In another aspect, the maximum norethindrone serum level may be up to about 8 times greater than the minimum norethindrone serum level. In yet another aspect, the maximum norethindrone serum level may be up to about 4 times greater than the minimum norethindrone serum level. In a further aspect, the maximum norethindrone serum level may be up to about 2.75 times greater than the minimum norethindrone serum level.

Contraceptive physiologic events can be sustained for varying amounts of time following progestin administration, depending on the dosage form, the nature of any penetration enhancer present, the amount of progestin in the formulation, etc. In one aspect, physiologic events may be sustained for a period of up to at least 168 hours. In another aspect, physiologic events associated with contraception may be sustained for a period from about 24 hours to about 168 hours. In yet another aspect, contraception may be sustained for a period of from about 24 hours to about 96 hours. In a further aspect, contraception may be sustained for a period of from about 48 hours to about 168 hours.

In accordance with another aspect of the invention, other progestins may be administered according to their additional potencies in amounts that are sufficient to provide a therapeutic effect equivalent to that of norethindrone. Those of ordinary skill in the art will readily recognize a number of mechanisms for determining the correct amount of a given progestin to substantially match the potency of a specific amount of norethindrone.

The exact amount of progestin to be included in the transdermal formulations of the present invention to achieve a contraceptively effective amount is also considered to be within the knowledge of those skilled in the art. Such a determination may depend again on the activity or potency of the specific progestin selected and physiological variations among women as to drug tolerance and general metabolic issues. Further, considerations for drug load may also be made in view of specifically desired properties for the transdermal formulation, such as size, delivery rate, and duration of administration, and may range from subsaturated to supersaturated concentrations. However, in one aspect, the amount of progestin may be from about 0.01% w/w to about 50% w/w of the formulation. In a further aspect, the amount of progestin may be from about 0.3% w/w to about 30% w/w of the formulation. In another aspect, the amount of progestin may be from about 1% w/w to about 15% w/w. In yet another aspect, the amount of progestin may be from about 2.5% w/w to about 12% w/w. In a further aspect, the amount of progestin may be about 5% w/w to about 10% w/w of the formulation. In an additional aspect, the progestin amount may be about 10% w/w of the formulation.

A number of pharmaceutically acceptable transdermal formulations and methods for administering progestin may be used for achieving the desired aspects of the present invention. The transdermal drug delivery system for the progestin may take a variety of well-known delivery formulations, including but not limited to transdermal patches such as adhesive matrix patches, liquid reservoir system (LRS) patches, transmucosal patches or tablets, and topical formulations, such as creams, lotions, ointments, gels, pastes, mousses, aerosols, sprays, suppositories, etc. In one general aspect, the transdermal drug delivery system can comprise a pharmaceutically acceptable carrier and a progestin for transdermal delivery.

When presented in the form of a transdermal patch, the transdermal drug delivery system of the present invention may include structural components, as known in the art. For example, in the case of an adhesive matrix patch, a distal backing can be laminated to a polymer layer. Such a distal backing defines the side of the matrix patch that faces the environment, i.e., distal to the skin or mucosa. The backing layer functions to protect the matrix polymer layer and the transdermal formulation, and to provide a layer that prevents loss of progestin to the environment. Thus, the material chosen for the backing should be compatible with the polymer layer, progestin, and any optional ingredient such as an enhancer, and should be minimally permeable to any components of the matrix patch. In one aspect, the backing can be opaque to protect components of the matrix patch from degradation from exposure to ultraviolet light. In another aspect, the backing can be transparent. Furthermore, the backing should be capable of binding to and supporting the polymer layer, yet should be pliable enough to accommodate the movements of a person using the matrix patch.

Suitable materials for the backing include, but are not limited to: metal foils, metalized polyfoils, composite foils or films containing polyester such as polyester terephthalate, polyester or aluminized polyester, polytetrafluoroethylene, polyether block amide copolymers, polyethylene methyl methacrylate block copolymers, polyurethanes, polyvinylidene chloride, nylon, silicone elastomers, rubber based polyisobutylene, styrene, styrene-butadiene and styrene-isoprene copolymers, polyethylene, and polypropylene. Additionally, the backing may include various foams, such as closed cell foams. Examples may include, without limitation, polyolefin foams, polyvinyl chloride foams, poly urethane foams, polyethylene foams, etc. In one aspect of the invention, the backing layer may have a thickness of about 0.0005 to 0.1 inch.

Further, a release liner may be temporarily provided upon the proximal side (side to adhere to the skin) of the adhesive layer. Such a liner provides many of the same functions as the backing layer, prior to adhesion of the patch to the skin. In use, the release liner is peeled from the adhesive layer just prior to application and discarded. The release liner can be made of the same materials as the backing layer, or other suitable films coated with an appropriate release surface.

In addition to containing the progestin, transdermal formulations of the present invention may also include one or more of a number of other additives, such as diluents, excipients, emollients, plasticizers, skin irritation reducing agents, or a mixture thereof. Such materials are pharmaceutically acceptable in that they are nontoxic, do not hinder drug delivery, and are not for any other reasons biologically or otherwise undesirable. Examples of such additional materials include water, mineral oils, silicone, inorganic gels, aqueous emulsions, liquid sugars, waxes, petroleum jellies, plasticizers, low molecular weight polymers, and a variety of other oils and polymeric materials. These types of components, as well as others not specifically recited, are well known in the art for inclusion in various transdermal formulations, and may be added as desired to the transdermal drug delivery system of the present invention in specific types and amounts in order to achieve a desired result. Additionally, many transdermal drug delivery formulations have a tendency to cause skin irritation after prolonged exposure to the skin, thus addition of a skin irritation reducing agent aids in achieving a composition that is better tolerated by the skin. In one aspect, the skin irritation reducing agent may be glycerin, as disclosed in U.S. Pat. No. 4,855,294, which is incorporated by reference in its entirety.

As described herein, the transdermal formulations of the present invention may also optionally include a permeation enhancer, or mixture of permeation enhancers. Useful permeation enhancers may include, without limitation, fatty acids, fatty acid esters, fatty alcohols, fatty acid esters of lactic acid or glycolic acid, glycerol tri-, di-, and monoesters, triacetin, short chain alcohols, and mixtures thereof. Specific species or combinations or species may be selected from the above listed classes of compounds by one skilled in the art, in order to optimize enhancement of the particular progestin employed. As more fully enumerated below, it has been found that sorbitan ester-type, lauryl-type, and polyol-type agents provide a significant penetration enhancing effect on norethindrone and norethindrone acetate. One skilled in the art would, however, understand that many other enhancers could be utilized in these formulations, and would thus be included within the scope of the present invention.

In one aspect of the present invention, the permeation enhancer is a sorbitan ester-type enhancer. Sorbitan ester-type enhancers are discussed in U.S. Pat. Nos. 5,227,169 and 5,212,199, which are incorporated by reference in their entireties. Exemplary sorbitan esters can be, without limitation, longchain sorbitan monoesters such as sorbitan monooleate and sorbitan monolaurate.

In another aspect, the permeation enhancer included in the transdermal formulation may be a lauryl-type enhancer. A variety of lauryl-type enhancers may be suitable for use in the present invention. However, in one aspect the lauryl-type enhancer used may include without limitation, lauryl alcohol, 1-lauryl-2-pyrrolidone, and mixtures thereof. In another aspect, the enhancer may be a mixture of lauryl alcohol in an amount of about 5% w/w and 1-lauryl-2-pyrrolidone in an amount of about 3% w/w. In yet another aspect, the permeation enhancer may be a polyol-type enhancer. Further, a variety of polyol-type enhancers may be suitable for use in the present invention. However, in one aspect, the polyol-type enhancer used may be dipropylene glycol.

The specific sorbitan ester-, lauryl-, or polyol-type enhancer, and the amount thereof, may be selected by one of ordinary skill in the art depending on a specific result to be achieved. However, as a general matter, the amount of enhancer included in the transdermal formulation may be from about 0.01% w/w to about 50% w/w of the formulation. In a more detailed aspect, the amount of enhancer may be from about 3% w/w to about 15% w/w of the formulation. In a further aspect, the amount of enhancer may be about 10% w/w of the formulation. In an additional aspect, the amount of enhancer may be about 5% w/w of the formulation.

In yet another aspect, the permeation enhancer in the transdermal formulation may be isopropyl myristate (IPM). IPM can be included as the sole enhancer, or the transdermal formulation can include IPM and at least one other enhancer, such as, without limitation, lauryl alcohol, sorbitan monooleate, or dipropylene glycol. In one particular aspect of the invention, the enhancer may be a combination of lauryl alcohol and isopropyl myristate. A more detailed discussion of permeation enhancer combinations of lauryl alcohol and isopropyl myristate can be found in Applicant's copending U.S. Patent Application No. 60/705,289 filed on Aug. 3, 2005 entitled "Formulations and Methods for Enhancing the Transdermal Penetration of a Drug," which is incorporated herein by reference.

In one general aspect, the transdermal drug delivery system of the present invention can comprise a pharmaceutically acceptable carrier intended to contain the progestin and other optional components. A number of pharmaceutically acceptable carriers are known to those of ordinary skill in the art and may be used in connection with the present invention.

The pharmaceutically acceptable carrier of an LRS patch may be of any suitable viscous material known to those skilled in the art of transdermal drug delivery. Such carriers are typically a fluid of desired viscosity, such as a gel or ointment, which is formulated for confinement in a reservoir having an impermeable backing and a skin contacting permeable membrane, or membrane adhesive laminate providing diffusional contact between the reservoir contents and the skin. Such a viscous carrier may contain both the progestin to be transdermally delivered as well as other optional components of the transdermal formulation. LRS patches are those described or referred to in U.S. Pat. Nos. 4,849,224, and 4,983,395, which are hereby incorporated by reference in their entirety.

The present invention contemplates various structural types of transdermal matrix patches. For example, monolithic systems where the progestin is contained directly in a single pressure sensitive adhesive layer, as well as systems containing one or more polymeric reservoirs in addition to the pressure sensitive adhesive layer may be utilized. In aspects comprising systems having multiple layers/laminates, a rate controlling member may be included. Generally, a rate controlling member is located between a reservoir layer and the skin. In those aspects including a delivery layer and a reservoir layer, the rate controlling member may be adhered between a proximal side of the reservoir layer, and a distal side of the delivery layer. The rate controlling member is provided for the purpose of metering, or controlling, the rate at which drug and/or permeation enhancer migrates from the storage layer into the delivery layer. As noted herein, in one aspect of the present invention, a permeation enhancer may be used to increase the delivery rate of the drug, and thus may also be used to vary other parameters, such as patch size, etc.

In one aspect, the pressure-sensitive adhesive of the pharmaceutically acceptable carrier can be suitable for long-term (e.g., greater than 1 day, may be about 3-4 days, or longer such as 1-4 weeks) contact with the skin. In another aspect, the pressure-sensitive adhesive of the carrier is suitable for a short-term administration (e.g., for a few minutes to a few hours, less than or equal to 1 day). Such adhesives must be physically and chemically compatible with the progestin and any optional enhancer present, and with any carriers and/or vehicles or other additives incorporated into the formulation. In one aspect of the invention, the adhesives of the pharmaceutically acceptable carrier can include polymeric adhesives. Example of such adhesives can include without limitation, acrylic adhesives including cross-linked and uncross-linked acrylic copolymers; vinyl acetate adhesives; natural and synthetic rubbers including polyisobutylenes, neoprenes, polybutadienes, and polyisoprenes; ethylenevinylacetate copolymers; polysiloxanes; polyacrylates; polyurethanes; plasticized weight polyether block amide copolymers, and plasticized styrene-rubber block copolymers or mixtures thereof. In yet another aspect of the invention, contact adhesives for use in the pharmaceutically acceptable carrier layer are acrylic adhesives, such as DUROTAK™ 87-2888 adhesive (National Starch & Chemical Co., Bridgewater, N.J.); and polyisobutylene adhesives such as ARCARE® MA-24 (Adhesives Research, Glen Rock, Pa.) and ethylene vinyl acetate copolymer adhesives. Those of ordinary skill in the art will appreciate that the specific type and amount of adhesive polymer used may be selected depending upon the desired specific characteristics of the final product. However, in one aspect, the amount of adhesive polymer in the adhesive matrix layer may be at least about 50% w/w of the adhesive layer. In another aspect, the amount may be at least about 60% w/w of the adhesive layer. In yet another aspect, the amount may be at least about 85% w/w of the adhesive layer. In a further aspect, the amount may be at least about 90% w/w of the adhesive layer. In an additional aspect, the amount may be from about 50% w/w to about 95% w/w of the adhesive layer.

In one aspect of the present invention, the carrier can be a biocompatible polymer. In another aspect, the carrier is an adhesive such as a polymeric adhesive matrix. In yet another aspect, the polymeric adhesive may be an acrylic polymer, such as an acrylic pressure sensitive adhesive. The carrier, in some aspects, may contain both the progestin to be transdermally delivered, and a permeation enhancer or other optional components.

The transdermal formulations of the present invention can also be provided with pharmaceutical carriers that improve the stability of progestins during long-term storage. Such compositions may comprise ethylhexylacrylate polymers, or other carriers that do not contain or form acid functional groups upon storage, as described in U.S. Pat. No. 5,780, 050, which is incorporated by reference herein. Methods for providing such hormones to females, as well as males, are also well known. See, U.S. Pat. Nos. 5,460,820, 5,152,997, and 5,783,208, which are incorporated by reference herein. It is appreciated that using the disclosure of the present invention, one skilled in the art can readily accomplish the objective of the above-referenced patents.

The formulations of the present invention can include sustained release formulations that administer therapeutically effective amounts of a progestin over an extended period of time. However, in one aspect, the sustained delivery period of the progestin may be for at least about 7 days. In another aspect, the sustained delivery period may be at least about 5 days. In a further aspect, the sustained delivery period may be at least about 3 days. In yet another aspect, the period may be about 24 hours.

In addition to the methods of providing progestin only contraception to minimize breakthrough bleeding side effects associated with progestin-only contraception, the present invention includes a kit for providing the progestin only contraception according to the methods disclosed herein. The kit can comprise a transdermally administrable formulation having a contraceptively effective amount of a single progestin as the sole active hormonal agent, and instructions describing a method of using the transdermally administrable formulation. The transdermal formulation can utilize the progestins, optional enhancers, dosage forms, and other transdermal components described herein.

EXAMPLES

The following examples of progestin-only contraceptive formulations are provided to promote a more clear understanding of certain embodiments of the present invention, and are in no way meant as a limitation thereon.

Example 1

Transdermal matrix systems containing norethindrone acetate can be made as follows. The solids contents of an acrylic adhesive solution, (DUROTAK™ 87-2888, National Starch) are determined by placing Small amounts into pre weighed aluminum dishes which are then put in a convection oven (Model A4718-Q, Blue M) at 75° C. overnight. Following evaporation of the solvents, the weight of the dry adhesive is obtained and the solids content calculated as a ratio of the dry to wet weight. The adhesive 87-2888 contains approximately 32-35% solids and is used undiluted. Known quantities of the adhesive are weighed into glass bottles based on previously determined solids content. An appropriate quantity of norethindrone acetate (NEA) is added to the liquid adhesive in each bottle to give about a 5% w/w NEA concentration upon drying. The bottles are capped and sealed with parafilm and rotated until all the NEA is dissolved. An appropriate amount of sorbitan monooleate (SMO) enhancer is added to the bottles containing the NEA in adhesive to give the desired compositions having about 10% w/w SMO enhancer upon drying. Each bottle is again tightly capped, sealed with parafilm and rotated overnight during which time the NEA and the enhancer dissolve to yield a clear solution.

An appropriate amount of the composition (about 10 g) is then placed onto the high release side of a silicone release-coated 3 Mil thick polyester (PET) liner (Loparex Inc., 10393S) and manually cast with a 10 Mil gap casting knife. Each cast is placed in a convection oven (Model A4718-Q, Blue M) at 75° C. for 15 minutes. After drying, each cast is then laminated with a 3 Mil polyethylene (PET) monolayer backing film (3M™, COTRAN™ 9720). The cast and backing film can then be cut to provide a proper delivery dosage, namely 22 cm$^2$ for 0.2 mg/day and 33 cm$^2$ for 0.3 mg/day patches.

Example 2

Transdermal matrix systems containing norethindrone acetate can also be made as follows. The solids contents of an acrylic adhesive solution, (DUROTAK™ 87-900A) are determined by placing small amounts into pre-weighed aluminum dishes which are then put in a convection oven (Model A4718-Q, Blue M) at 75° C. overnight. Following evaporation of the solvents, the weight of the dry adhesive is obtained and the Solids content calculated as a ratio of the dry to wet weight.

The adhesive 87-900A contains approximately 40-44% solids and is used undiluted. Lauryl alcohol is a solid at room temperature and has to be melted by heating a small quantity held in a glass jar in a water bath prior to use. For each casting solution being prepared, the appropriate amount of soluble polyvinylpyrrolidone (PVP) K-12 to yield 10% w/w in the dried film is weighed directly into a jar and the minimum amount of absolute ethanol calculated to completely dissolve the PVP is added to the jar. After dissolving the PVP based on the previously determined solids content, a known volume of the adhesive is weighed into the jar and, appropriate amounts of Norethindrone acetate (NEA), lauryl alcohol (LA), isopropyl myristate (IPM) (with the appropriate overages) are added to provide the desired compositions upon drying 10% w/w NEA, 5% w/w LA, 5% w/w IPM and 10% w/w PVP-K12. The bottles are tightly capped, sealed with parafilm and rotated over night during which time all the ingredients dissolve to yield a translucent solution.

A small amount of the formulation (about 10 g) is placed onto a fluoropolymer coated 3 Mil thick polyester (PET) liner (3M™, SCOTCHPAK™, 1022) and manually cast with a 10 mil gap casting knife. The cast is placed in a convection oven (Model A4718-Q, Blue M) at 75° C. for 15 minutes. After drying, the cast is laminated with the polyester side of a 2 Mil (PET/EVA) laminate backing film (3M™, SCOTCHPAK™, 9739). The cast and backing film can then be cut to appropriate sizes to provide a proper delivery dosage, 0.2 mg/day and 0.3 mg/day patches.

Example 3

A clinical trial using the transdermal formulation of Example 1 was conducted for the purposes of comparing such formulations with oral progestin-only contraceptive tablets (NOR QD®, Watson Pharmaceuticals, Inc.) Volunteer subjects were subjected to a screening and baseline period consisting of a 4-week washout of previous contraceptive treatment, if necessary, followed by approximately a one month baseline evaluation period (cycle 1) which consisted of one full menses cycle to determine eligibility for participating in the study. Eligibility was based on whether a subject ovulated (serum progesterone >3 ng/ml) and had a favorable cervical mucus score (10) during cycle 1. Subjects who qualified for entry into the study were randomized into two 12-week study groups:

once weekly application to the abdomen of 0.3 mg/day formulation of Example 1 for 12 consecutive weeks starting on the first day of bleeding of the first menstrual cycle following randomization; and once daily oral administration of 0.35 mg NOR QD® (norethindrone-only formulation) for 12 consecutive weeks starting on the first day of bleeding of the first menstrual cycle following randomization.

A third study group was also established, the results of which are not included herein. A treatment period consisted of 12-week study divided into three cycles, namely cycles 2-4. Each cycle was approximately 4 weeks in duration, beginning on the first day of menstrual bleeding for a give cycle.

Example 4

Plasma norethindrone (NE) concentration measurements were performed on the study groups of Example 3 to determine the peak and trough levels of NE during the third month of treatment, Cycle 4. For the oral 0.35 mg NOR QD® group, trough NE plasma concentration levels were collected prior to the Subjects taking their morning dose, and peak NE plasma concentration levels were collected one hour following dosing. For the 0.3 mg/day NOR TD™ group, peak and trough NE plasma concentration values were determined by comparing the date/time of the concentration to the date/time of the last transdermal patch application. For example, blood NE samples were considered peak concentration levels if the blood was collected >24 hours and <96 hours from the time of the last transdermal patch application. If however, the difference between when the blood NE sample was collected and the time of the last transdermal patch application was <24 hours or was between 96 and 168 hours, the concentration level was considered trough. Plasma NE concentrations are summarized for each treatment group in Table 1.

TABLE 1

Plasma NE concentrations summarized for each treatment group
Plasma NE concentrations (pg/mL)

|  | 0.3 mg/day NOR TD ™* | 0.35 mg NOR QD ®** |
|---|---|---|
| Peak | 549.8 | 2721.9 |
| Trough | 367.6 | 551.2 |

*80 subjects
**79 subjects

The mean peak NE levels for the 0.3 mg/day NOR TD™ dose group is similar to levels (600 pg/mL) that are thought to be required to consistently inhibit ovulation when using subdermal implants of NEA. As can be seen in Table 1, daily ingestion of an oral NE formulation produces significantly higher plasma NE concentrations than the transdermal NE formulation. Moreover, the difference between peak and trough associated with the transdermal formulation is much less than the difference associated with the oral formulation.

Example 5

The portion of each group that did not ovulate was during the treatment is shown in Table 2. A direct quantitative assessment was obtained by measuring serum progesterone levels. Non-ovulation was defined as serum progesterone levels of ≤3 ng/mL.

TABLE 2

The proportion of subjects who did not ovulate
Ovulation

|  | 0.3 mg/day NOR TD ™* | 0.35 mg NOR QD ®** |
|---|---|---|
| Ovulated | 55% | 49% |
| Did not ovulate | 45% | 51% |

*80 subjects
**79 subjects

The 95% confidence interval lower limit for the 0.3 mg/day NOR TD™ treatment group was -18.6%, and is therefore within a 20% equivalence bound indicating that the two treatment groups are considered equivalent.

Example 6

Cervical mucus samples were collected between Days 11 and 17 of Cycle 4 and scored according to *WHO Laboratory Manual for the Examination of Human Semen and Sperm-Cervical Mucus Interaction*, ($4^{th}$ ed., Cambridge University Press, 1999), which is incorporated herein by reference. Variables evaluated included volume, spinnbarkeit, consistency, cellularity, and ferning. The scale for each variable ranged from 0 to 3, allowing a maximum total score of 15. The score for each variable was totaled to produce the cervical mucus score, which could range from 0 to 15. Using the scoring system from the WHO lab manual, a score ≥10 was used to indicate cervical mucus conditions favorable for sperm penetration and a score <10 was used to indicate unfavorable mucus conditions for sperm penetration. The results of this evaluation are shown in Table 3.

TABLE 3

A comparison of cervical mucus status
Cervical Mucus Status (Cycle 4)

|  | 0.3 mg/day NOR TD ™* | 0.35 mg NOR QD ®** |
|---|---|---|
| % Favorable | 11% | 8% |
| % Unfavorable | 89% | 92% |

*80 subjects
**79 subjects

The 95% confidence interval lower limit for the 0.3 mg/day NOR TD™ treatment group was −12.1%, and is therefore within a 20% equivalence bound indicating that the two treatment groups are considered equivalent.

Example 7

Subjects in the treatment groups of Example 3 were evaluated for any breakthrough bleeding that occurred during the three cycles. A number of subjects were included in this evaluation that were disqualified prior to the evaluations in Examples 4-6. Breakthrough bleeding or intermenstrual bleeding was defined as any bleeding or spotting occurring during the menstrual cycle, excluding contiguous bleeding with menses. Breakthrough bleeding was categorized using the following criteria:
  none
  spotting (≤1 sanitary pad/tampon used)
  bleeding (≥2 sanitary pad/tampons used)
Results from the breakthrough bleeding studies are contained in Tables 4 and 5.

TABLE 4

A comparison of the percentage of women that experienced breakthrough bleeding (spotting)
Breakthrough Bleeding: Spotting

|  | Cycle 2 | Cycle 3 | Cycle 4 |
|---|---|---|---|
| 0.3 mg/day NOR TD ™* | 13.6% | 17.8% | 18.4% |
| 0.35 mg NOR QD ®** | 17.9% | 18.4% | 21.9% |

*112 subjects
**113 subjects

TABLE 5

A comparison of the percentage of women that experienced breakthrough bleeding (bleeding)
Breakthrough Bleeding: Spotting

|  | Cycle 2 | Cycle 3 | Cycle 4 |
|---|---|---|---|
| 0.3 mg/day NOR TD ™* | 20.0% | 23.4% | 20.4% |
| 0.35 mg NOR QD ®** | 14.3% | 27.2% | 34.4% |

*112 subjects
**113 subjects

As can be seen from these data, the incidence of breakthrough bleeding was lower in the 0.3 mg/day NOR TD™ group than the oral 0.35 mg NOR QD® group, particularly for bleeding during cycle 4.

Examples 5 and 6 demonstrate that the 0.3 mg/day NOR TD™ and the 0.35 mg NOR QD® formulations may be therapeutically equivalent because they appear to provide equivalent levels of contraceptive protection as demonstrated by the similarities observed in the study populations regarding ovulation and cervical mucus status.

Given this apparent dose equivalence and similar contraceptive effect between the 0.30 mg/day transdermal and the 0.35 mg oral formulations, a surprising relationship appears between the progestin dosage form and the incidence of breakthrough bleeding in the study populations shown in Example 7. Specifically, transdermal delivery of the NEA-only formulation caused overall fewer incidents of breakthrough bleeding than the oral NE-only formulation. It is possible that the higher incidence of breakthrough bleeding in the group taking the 0.35 mg NOR QD® oral formulation may be a result of the significantly higher peak NE serum levels observed as compared to the 0.3 mg/day NOR TD™ transdermal formulation, as shown in Example 4. Thus the higher peak serum level of NE as a result of taking an oral NE formulation may be associated with the higher incidence of side effects. Moreover, as shown in Table 1, the difference between peak and trough associated with the transdermal formulation is much less than the difference associated with the oral formulation. As such, NE serum level rise and fall rapidly throughout a 24 hour period. This rapid change may also account for the differences in breakthrough bleeding side effects observed between the oral and transdermal formulations.

Regardless of the method of action, however, it is apparent from these data that the transdermal NEA-only formulation is superior to the oral NE-only formulation because, while both attain substantially similar contraceptive effects, the transdermal formulation further minimizes side effects such as breakthrough bleeding and reduce the risk of dosage non-compliance, and therefore increases the overall efficacy of the contraceptive regimen.

It is to be understood that the above-described compositions and modes of application are only illustrative of preferred embodiments of the present invention.

Numerous modifications and alternative arrangements may be devised by those skilled in the art without departing from the spirit and scope of the present invention and the appended claims are intended to cover such modifications and arrangements.

Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A transdermal patch comprising:
   a) norethindrone as the sole hormonal active agent or a combination of norethindrone and norethindrone acetate as the sole hormonal active agents in an amount of from 1% to 15% w/w; and
   b) a permeation enhancer comprising (i) isopropyl myristate and (ii) lauryl alcohol,
   wherein the transdermal patch is formulated to minimize adverse side effects associated with progestin-only contraception by providing:
      a) a minimum norethindrone serum level of at least 300 pg/ml from 24 hours to 168 hours following application of the patch to an outer skin surface; and
      b) a maximum norethindrone serum level of less than 2400 pg/ml from about 24 to 96 hours following application of the patch to the outer skin surface,
   wherein the side effects are selected from the group consisting of strokes, myocardial infarctions, embolisms, breakthrough bleeding and combinations thereof.

2. The transdermal patch of claim 1 wherein the permeation enhancer is present in an amount of from 0.01% to 50% w/w.

3. The transdermal patch of claim 2 wherein the permeation enhancer is present in an amount of from 3% to 15% w/w.

4. The transdermal patch of claim 1, wherein the sole hormonal active agents are present in an amount of from 2.5% to 12% w/w.

5. The transdermal patch of claim 4, wherein the sole hormonal active agents are present in an amount of from 5% to 10% w/w.

6. The transdermal patch of claim 1, wherein the sole hormonal active agents are present in an amount of 10% w/w.

7. The transdermal patch of claim 1, wherein the permeation enhancer is present in an amount of 5% w/w.

8. The transdermal patch of claim 1, wherein the permeation enhancer is present in an amount of 10% w/w.

9. The transdermal patch of claim 1, wherein the sole active hormonal agent is norethindrone.

10. The transdermal patch of claim 1, wherein the sole active hormonal agent is a combination of norethindrone and norethindrone acetate.

11. The transdermal patch of claim 1, wherein the transdermal patch is formulated to deliver the sole active hormonal agent in an amount of 0.2 mg/day.

12. The transdermal patch of claim 1, wherein the transdermal patch is formulated to deliver the sole active hormonal agent in an amount of 0.25 mg/day.

13. The transdermal patch of claim 1, wherein the transdermal patch is formulated to deliver the sole active hormonal agent in an amount of 0.3 mg/day.

14. The transdermal patch of claim 1, wherein the transdermal patch is formulated to deliver the sole active hormonal agent in an amount of 0.35 mg/day.

15. The transdermal patch of claim 1, wherein the transdermal patch is a matrix patch.

16. The transdermal patch of claim 15, wherein the matrix patch comprises an acrylic polymer adhesive.

17. The transdermal patch of claim 1, wherein the transdermal patch is a transdermal liquid system patch.

18. The transdermal patch of claim 1, wherein the transdermal patch further comprises diluents, emollients, plasticizers, skin irritation reducing agents, or a mixture thereof.

19. The transdermal patch of claim 18, wherein the transdermal patch includes a skin irritation reducing agent and wherein the skin irritation reducing agent is glycerin.

20. The transdermal patch of claim 1, wherein the sole active hormonal agent is a combination of norethindrone and norethindrone acetate, which are present in an amount of from 2.5% to 12% w/w; the permeation enhancer is present an amount of from 3% to 15% w/w; and the patch further comprises a diluent, an emollient, a plasticizer, a skin irritation reducing agent, or a mixture thereof.

21. The transdermal patch of claim 20, wherein the patch is a matrix patch and comprises an acrylic polymer adhesive.

* * * * *